United States Patent
Monastra et al.

[11] Patent Number: 6,097,980
[45] Date of Patent: Aug. 1, 2000

[54] QUANTITATIVE ELECTROENCEPHALOGRAPHIC (QEEG) PROCESS AND APPARATUS FOR ASSESSING ATTENTION DEFICIT HYPERACTIVITY DISORDER

[76] Inventors: Vincent J. Monastra, 927 S. Pines Dr., Endwell, N.Y. 13760; Joel F. Lubar, 6423 Deane Hill Dr., Knoxville, Tenn. 37919

[21] Appl. No.: 09/220,719

[22] Filed: Dec. 24, 1998

[51] Int. Cl.[7] ................................................... A61B 5/04
[52] U.S. Cl. ............................................................ 600/544
[58] Field of Search ............................................ 600/544

[56] References Cited

U.S. PATENT DOCUMENTS

| | | | |
|---|---|---|---|
| 5,176,145 | 1/1993 | Ryback et al. ........................... | 600/544 |
| 5,550,021 | 8/1996 | Blum et al. .................................. | 435/6 |

OTHER PUBLICATIONS

Zametkin, A.J., Ernst, M., & Silver, R. (1998). Laboratory and diagnostic testing in child and adolescent phychiatry: A review of the past 10 years. *Journal of the American Academy of Child and Adolescent Psychiatry*, 37, 464–472.

Barkley, R.A., McMurray, M.B., Edelbrock, C.S., & Robbins, K. (1990). The side effects of Ritalin: A systematic placebo controlled evaluation of two doses. *Pediatrics*, 86 184–192.

Swanson, J.M., McDurnett, K., Christian, D.L., & Wigal, T. (1995). Stimulant medications and the treatment of children with ADHD. In T.H. Ollendick & R.J. Prinz (Eds.) *Advances in Clinical Child Psychology* (vol. 17, pp. 265–322). New York: Plenum.

Achenbach, T.M., & Edelbrock, C.S. (1983). *Manual for the Child Behavior Profile and Child Behavioral Checklist* Burlington, VT: Author.

Connors, C.K. (1969). A teacher rating scale for use in drug studies with children. *American Journal of Psychiatry* 126, 884–888.

(List continued on next page.)

*Primary Examiner*—Max Hindenburg
*Assistant Examiner*—Ryan Carter
*Attorney, Agent, or Firm*—Salzman & Levy

[57] ABSTRACT

A simplified, quantitative electroencephalographic (QEEG) technique and apparatus for testing and assessing individuals for Attention Deficit Hyperactivity Disorder (ADHD) is described. The simplified procedure and apparatus is consistent with emerging neuroanatomical models of the etiology of ADHD, makes the testing affordable to the public, and allows for practitioners to conduct the testing on an outpatient basis within their offices. The process comprises a new scanning method that obtains quantitative EEG data from an electrode placed at a single, active cranial site (Cz, the vertex). Multiple short periods (90 seconds) of digitized EEG are obtained. The electrophysiological power in two frequency bands (theta: 4–8 Hz; beta: 13–21 Hz) is examined. A computer that is programmed with the capacity to conduct a Fast Fourier Transformation selects and statistically analyzes the power in these specific EEG frequency bands. A baseline neurometric index is obtained by calculating the ratio of the electrophysiological power recorded within the theta band by that recorded in the beta band while the individual maintains an eyes open, fixed gaze. Thereafter, the individual being tested for ADHD is evaluated under conditions requiring attentive behavior (reading, listening, drawing). A theta/beta power ratio is calculated for each of these tasks. Finally, an average of the power ratios across the baseline, reading, listening and drawing tasks is calculated and an Attentional Index is obtained and compared to a database obtained through the evaluations of a normative sample of individuals not having ADHD or any other neurological disorder. The assessment of the presence and severity of ADHD is determined from this comparison.

13 Claims, 3 Drawing Sheets

OTHER PUBLICATIONS

DuPaul, G.J. (1990). *The ADHD Rating Scale: Normative Data Reliability and Validity*. Worchester: University of Massachusetts Medical Center.

Sanford, J.A. (1994). *IVA Manual*. Richmond, VA: Braintrain.

Blondis, T.A., Accardo, P.J., & Snow, J.H. (1989). Measures of attention deficit: I. Questionnaires. *Clinical Pediatrics*, 28, 222–228.

Corkum, P.V., & Siegel, L.S. (1993). Is the Continuous Performance Task a valuable research tool for use with children with attention–deficit–hyperactivity disorder? *Journal of Child Psychology & Psychiatry & Allied Disciplines*, 34, 1217–1239.

Casey, B.J., Castellanos, F.X., Giedd, J.N., Marsh, W.L., Hamburger, S.D., Schubert, A.B., Vauss, Y.C., Vaituzis, A.C., Dickstein, D.P., Sarfatti, S.E., & Rapoport, J.L. (1997). Implication of right frontostriatal circuitry in response inhibition and attention–deficit/hyperactivity disorder. *Journal of the American Academy of Child and Adolescent Psychiatry*, 36, 374–383.

Zametkin, A.J., Nordahl, T.E., Gross, M., King, A.C., Semple, W.E., Rumsey, J., Hamburger, S., & Cohen, R.M. (1990), Cerebral glucose metabolism in adults with hyperactivity of childhood onset. *New England Journal of Medicine*, 323, 1361–1366.

Amen, D.G., Paldi, J.H., & Thisted, R.A. (1993). Evaluating ADHD with brain SPECT imaging. *Journal of the American Academy of Child and Adolescent Psychiatry*, 32, 1081–1091.

Hynd, G.W., Hern, K.L., Novey, E.S., Eliopulos, D., Marshall, R., Gonzalez, J.J., & Voeller, K.K. (1993). Attention deficit hyperactivity disorder and asymmetry of the caudate nucleus. *Journal of Child Neurology*, 8, 339–347.

Semrud–Clikeman, M., Filipek, P.A., Biederman, J., Steingard, R., Kennedy, D., Renshaw, P., & Bekken, K. (199 Attention–deficit hyperactivity disorder: Magnetic resonance imaging morphometric analysis of the corpus callosum. *Journal of the American Academy of Child and Adolescent Psychiatry*, 33, 875–881.

Castellanos, F.X., Giedd, J.N., Eckburg, P., Marsh, W.L., Vaituzis, C., Kaysen, D., Hamburger, S.D., & Rapoport, J.L. (1994). Quantitative morphology of the caudate nucleus in attention deficit hyperactivity disorder. *American Journal of Psychiatry*, 151, 1791–1796.

Castellanos, F.X., Giedd, J.N., Marsh, W.L., Hamberger, S.D., Vaituzis, A.C., Dickstein, D.P., Sarfatti, S.E., Vauss, Y.C., Snell, J.W., Lange, N., Kaysen, D., Krain, A.L., Ritchie, G.F., Rajapkse, J.C. & Rapoport, J.L. (1996). Quantitative brain magnetic resonance imaging in attention–deficit hyperactivity disorder. *Archives of General Psychiatry* 53, 607–616.

Mann, C.A., Lubar, J.F., Zimmerman, A.W., Miller, B.A. & Nuenchen, R.A. (1992). Quantitative analysis of EEG in boys with attention deficit/ hyperactivity disorder (ADHD). A controlled study with clinical implications. *Pediatric Neurology*, 8, 30–36.

Chabot, R.A., & Serofontein, G. (1996). Quantitative electroencephalographic profile of children with attention deficit disorder. *Biological Psychiatry*, 40, 951–963.

Monatstra, V.J., Lubar, J.F., Linden, M., VanDeusen, P., Green, G., Wing, W., Phillips, A., & Fenger, T.N. (1998). Assessing ADHD via quantitative electroencephalographic: An initial validation study. *Neuropsychology*, In press.

Lubar, J.F.,(1997). Neocortical dynamics: Implications for understanding the role of neurofeedback and relaed techniques for the enhancement of attention. *Applied Psychophysiology and Biofeedback*, 22, 111–126.

Sterman, M.B., (1996) .Physiological origins and functional correlates of EEG rhythmic activities: Implications for self regulation. *Biofeedback and Self–Regulation*, 21, 3–33..

Lubar, J.R., Bianchini, K.T., Calhoun, W.H., Lambert, E.W., Bordy, Z.H., & Shabsin, H.W. (1985) . Spectral analysis of EEG differences between children with and without learning disabilities. *Journal of Learning Disabilities*, 18, 403–408.

Cooley, J.W., & Tukey, J.W. (1965) .An algorithm for the machine calculation of complex Fourier series. *Mathematica of Computation*, 19, 267–301.

Lubar, J.F., Swartwood, M.O., Swartwood, J.N., & Timmermann, D.L. (1996). Quantitative EEG and auditory event–relatedd potentials in the evaluation of attention–deficit/ hyperactivity disorder: Effects of methylphenidate and implications for neurofeedback training. *Journal of Psycheducational assessment* (Monograph: *Assessment of Attention–Deficit/Hyperactivity Disorders*, pp. 143–204).

Monatstra, V.J., Lubar. J.F., Linden, M., (1998) . Assessing ADHD via quantitative electroencephalographic: Test validation and reliability studoes. Presented at CH.A.D.D.'s Tenth Annual Conference, New York. Paper in preparation.

Amen, D.G., & Carmichael, B.A. (1975). Oppositional children similar to OCD on SPECT: Impliications for treatment. *Journal of Neuropathy*, 2, 1–7.

Hollander, E. (1992). Hyperfrontality and serotonin in OCD. Presented at the Annual Meeting of the American Psychiatric Association.

Machlin, S.R., Harris, G.J., Peralson, G.D. (1991). Elevated medial–frontal cerebral blood flow in obsessive–compulsive patients: A SPECT study. *American Journal of Psychiatry*, 148, 1240–1242.

Nordahl, T.E., Benkelfat, C., & Semple, W.E. (1989). Cerebral glucose metabolic rates in obsessive compulsive disorder. *Neuropsychopharmacology*, 2, 23–38.

Machlin, S.R., Harris, G.J., Peralson, G.D. (1991). Elevated medial–frontal cerebral blood flow in obsessive–compulsive patients: A SPECT study. *American Journal of Psychiatry*, 148, 1240–1242.

QUANTITATIVE ELECTROENCEPHALOGRAPHIC (QEEG) PROCESS AND APPARATUS FOR ASSESSING ATTENTION DEFICIT HYPERACTIVITY DISORDER

FIELD OF THE INVENTION

The present invention relates to the diagnosis of individuals with Attention-Deficit Hyperactivity Disorder (ADHD) and, more specifically, to a simplified quantitative electroencephalographic (QEEG) process for assessing such patients.

BACKGROUND OF THE INVENTION

Attention Deficit Hyperactivity Disorder (ADHD) is a psychiatric disorder that has been characterized historically by the behavioral symptoms of inattention, impulsivity and hyperactivity. Estimates of the prevalence of this disorder range from five to fifteen percent of the school-aged population, making ADHD the most commonly diagnosed childhood psychiatric disorder [1]. The disorder occurs more commonly in males than in females, with ratios ranging from 4:1 to 9:1 [2]. Onset of the condition typically occurs prior to age seven.

Despite the prevalence of ADHD, there are no current laboratory measures considered useful in the diagnosis of ADHD [1, 2, 3]. Nevertheless, although there are no reliable tests to evaluate the assumed neurophysiological foundation of this disorder, stimulant medications like Ritalin, Adderall, Dexedrine and Cylert are routinely prescribed to millions of American children [1]. Adverse side effects including decreased appetite, insomnia, anxiety, irritability, and affective lability have been reported to occur in approximately 50% of the patients [4] with stomachaches and headaches reported in one third of the patients. In addition, estimates of the percentage of children responding to medication has been reported to be as low as 55–65% for children diagnosed with ADHD, Inattentive Type and 70–90% for ADHD, Combined Type [1]. A recently published review of studies of stimulant therapies [5] concluded that no positive clinical response was noted in 25 to 40% of the patients.

The frequency of adverse side effects and the limited efficacy of prescribed medications in approximately 50% of the children "diagnosed" with ADHD raises serious questions about the accuracy of current assessment procedures. The most common of the diagnostic procedures used in clinical practice include "interviews" and "behavioral rating scales." Such procedures are commonly utilized in evaluating psychiatric disorders since laboratory techniques are not available for the vast majority of conditions listed in the DIAGNOSTIC AND STATISTICAL MANUAL FOR MENTAL DISORDERS [2]. In assessing ADHD, behavioral rating scales such as the Child Behavioral Checklist [6], the Conners' Rating Scales [7], the ADHD Rating Scale [8] and the Attention Deficit Disorder Evaluation Scale [9] were developed to provide a database for comparing the behavioral observations of parents and teachers with "normative" populations. Similarly, continuous performance tests (CPTs), which measured capacity for vigilance and impulse control during visual and auditory tracking tasks [10, 11, 12], were developed to provide a more objective measure of the core symptoms of inattention and impulsivity.

While these measures were considered useful in the assessment process, particularly when combined with a thorough review of medical, developmental and family histories and an examination of intellectual functions and academic achievement, these tests could not be considered diagnostic for ADHD [1, 3]. Behavioral rating scales have limited diagnostic value due to a variety of rater biases [1, 13]. Similarly, the accuracy of CPTs is limited by the high rate of "false negative" scores [10, 11, 12, 14]. Consequently, in order to improve diagnostic accuracy, the development of additional assessment procedures appears necessary.

Overall, it appears that current procedures for medical examination are useful in differentiating ADHD from similar symptoms engendered by other physical disorders (e.g., thyroid disorders, anemia, hypoglycemia, allergies, diabetes). However, the absence of neurologically-based assessment procedures prevents physicians from examining the neurological causes of ADHD. Similarly, although conducting a thorough functional behavioral assessment at home and school can result in useful motivational strategies and instructional adaptations to promote the development and self-esteem of patients with a variety of behavioral disorders, such procedures do not target the neurological foundations of ADHD. This disconnection of treatment procedures from a coherent theoretical perspective regarding the etiology of ADHD is highly problematic, particularly when the most common form of treatment is the use of stimulant medications.

As with other medical conditions, a clear understanding of the causes of the illness or disorder is essential for the development of valid assessment procedures and effective, enduring treatments. During the past decade, multiple research teams, utilizing neuro-imaging techniques such as magnetic resonance imaging (MRI), positron emission tomography (PET) and single photon emission computed tomography (SPECT), have reported findings that support the hypothesis that anatomical and biochemical abnormalities of the pre-frontal cortex constitute the physical basis of ADHD [15, 16, 17, 18, 19, 20, 21].

More specifically, hypoperfusion and low metabolic activity in the pre-frontal and caudate nuclei regions and anatomical differences in the caudate nucleus, the cingulate gyrus and in the cerebellum have been observed in patients diagnosed with ADHD. Overall, these studies have provided initial evidence of the importance of the frontostriatal circuitry in understanding the neurological basis of ADHD.

As researchers proceeded to clarify the neuroanatomical structures implicated in ADHD, three research teams [22, 23, 24] sought to examine QEEG characteristics of patients diagnosed with ADHD. The rationale for application of the QEEG process is based on an understanding of the neuroanatomical basis of EEG patterns. As noted by Lubar [25], EEG activity arises from intracortical loops which are modulated by groups of cells in the thalamus. The "firing" of these cell groups (called "pacemakers") are responsible for the electrical "rhythms" or "wave forms" which are recorded by EEGs based on input from surface electrodes. Of particular interest to researchers examining patients diagnosed with ADHD are low frequency rhythms (4–8 Hz: "theta"), faster wave forms called "beta" (16–20 Hz) recorded in frontal and midline locations and SMR waves (12–16 Hz) recorded above the sensorimotor cortex. A series of studies by Sterman [26] clearly demonstrated the relationship between these specific electrical "wave forms" as recorded on the surface and the activity of the ventrobasal thalamus; and clarified that signals from the sensory pathways are conveyed to the cerebral cortex through relay nuclei in the thalamus. It is this region that has been identified as potentially critical in the manifestation of ADHD symptoms through neuro-imaging studies.

The common hypothesis shared by each of the research teams was that if cortical slowing was evident on PET and SPECT examinations, then such slowing would be evident during a QEEG assessment. The first two teams [22, 23] used a complex statistical analysis (discriminant function analysis) using recordings from multiple cortical locations and a variety of QEEG measures (e.g., electrophysiological power, absolute and relative power in the "theta" and "beta" frequencies, as well as measures of coherence and hemispheric symmetry). While both of these teams noted cortical slowing on QEEG examination and were able to identify patients with ADHD with a high degree of accuracy (85–95%), their procedure was criticized due to the complexity of the analysis and the significant probability that because of the multiplicity of QEEG measures analyzed, certain QEEG measures would show significant differentiation due to chance alone. In order to address these criticisms, a simplified QEEG process was developed by the present inventors.

This invention proceeds from the earlier work of one of the inventors [27] and an extensive series of studies conducted by the two inventors [42, 43]. The current process developed for assessing patients for ADHD is a simplified neurometric procedure. Like other researchers who have utilized a computerized power spectral analysis (PSA) to study patterns of cortical activation, this procedure involves the collection of multiple, short periods of digitized EEG which are subjected to a Fast Fourier Transformation (FFT) algorithm [28]. The FFT derived data are averaged over all trials for a given experimental condition. The overall electrophysiological power (pW) can then be determined for various frequency bands at the various active electrode sites. The current invention, however, simplifies the number of frequency bands and the number of active locations. It is based on an examination of the electrophysiological power produced within two frequency bands (4–8 Hz and 13–21 Hz) recorded at one active site (the vertex: Cz) with ear references.

Initially examined was the relationship between ADHD and a ratio of the electrophysiological output (pW) produced within the theta band (4–8 Hz) to that recorded at 13–21 Hz. This theta/beta power ratio was calculated from 19 locations as individuals completed the following tasks: eyes open baseline; eyes closed baseline; reading silently; completing visual-motor tasks; listening. Consistent with emerging neuroanatomical models of ADHD, it was hypothesized that evidence of excessive cortical slowing (i.e., a higher ratio of slow wave activity relative to "fast" EEG activity) would be noted in individuals diagnosed with ADHD. The results of this initial study supported the hypothesis. Significant group differences were noted in the theta/beta power ratios obtained at multiple cortical sites with Cz and Fz appearing the most promising for consideration in the development of an assessment procedure based on PSA.

Since the initial test of the validity of examining the theta/beta power ratio could be criticized for evaluating numerous cortical sites (i.e., at p<0.05; 1 of 20 sites would be expected to yield significant differences due to chance alone), further development of a neurometric process for assessing ADHD required simplification of the scanning procedure. Since earlier research [29] had indicated that QEEG recordings at Cz best differentiated ADHD from non-ADHD controls, this location was selected for further testing. In subsequently reported research [24], the inventors conducted a spectral analysis of the electrophysiological output (theta/beta power ratio) at a single, midline location (Cz) in 482 individuals to test the hypothesis that electrophysiological indicators of slowing in the prefrontal cortex could serve as a basis for differentiating patients with ADHD from non-clinical control groups.

Participants were classified into three groups (ADHD, Inattentive; ADHD Combined; Control) based on the results of medical examination, a standardized clinical interview, behavioral rating scales and a CPT. QEEG recordings were obtained during an eyes fixed baseline, as well as reading, listening and drawing tasks. Theta/beta power ratios were obtained for each of the four conditions and the mean ratio was calculated for each individual. Using the mean and standard deviation of the control group to develop "critical values" for cortical slowing, participants were classified into ADHD or control groups on the basis of their average theta/beta ratio. Classification as ADHD or Control on the basis of QEEG findings alone was consistent with group placement based on interview and psychometric data in 88% of the cases. The sensitivity of the QEEG-derived "Attentional Index" was 86%; the specificity was 98%. Extensive examination of this process has been conducted [30] and is reported in "Test Results" hereinbelow.

Based on the results of previous QEEG studies using PSA, the present inventors developed and tested a simplified neurometric procedure for use in the assessment of ADHD. Due to the high cost and level of complexity of other types of neuro-imaging techniques, the development of a simplified scanning process is desirable to provide essential physiological data to physicians at a cost affordable to the general public. In addition, by reducing the complexity and cost of equipment needed for the scan, medical practitioners are now able to complete the evaluation in their private offices.

SUMMARY OF THE INVENTION

In accordance with the present invention, there is provided a simplified QEEG process for assessing individuals suspected of having Attention Deficit Hyperactivity Disorder. The simplified procedure makes the testing affordable to the public and allows for practitioners to conduct the testing within their offices. The process comprises a new scanning method that obtains quantitative EEG data from an electrode placed on a single, Cz cranial site with two ear references. Multiple short periods (90 seconds) of digitized QEEG are obtained. The electrophysiological power is examined in two frequency bands: theta (4–8 Hz) and beta (13–21 Hz). A computer that is programmed with a Fast Fourier Transformation selects and statistically analyzes these specific EEG band passes. Four, 90 second data collection periods are conducted. During the First Condition, the patient maintains an eyes open fixed gaze, data is recorded, artifacted (to remove any two second periods containing excessive muscular or ocular movements), and statistically analyzed in order to yield a ratio of power produced in the theta band divided by that produced in the beta band. The same is done while the patient reads silently (Condition 2), listens to reading (Condition 3) or copies geometric figures (Condition 4). An average theta/beta power ratio is calculated over the four conditions. This average is then compared with a normative database for age peers without ADHD. The assessment of the presence and severity of ADHD in the individual is determined based on this comparison.

In summary, the primary objectives of this invention are:
a) to provide an improved, simplified, quantitative method for assessing ADHD that is based on reliable QEEG procedures and is consistent with emerging neuroanatomical models of the etiology of ADHD;
b) to provide a QEEG procedure that enables practitioners to conduct evaluations for ADHD in an office setting; and c) to provide a low cost procedure for conducting an evaluation for patients with ADHD that is affordable to the general public.

BRIEF DESCRIPTION OF THE DRAWINGS

A complete understanding of the present invention may be obtained by reference to the accompanying drawings, when considered in conjunction with the subsequent detailed description, in which.

DETAILED DESCRIPTION OF THE PREFERRED EMBODIMENT

Generally speaking, the present inventive method for testing and assessing ADHD is based upon earlier findings that indicated that the highest degree of differentiation between ADHD patients and non-ADHD controls was noted at the vertex [29]. Therefore, the Cz cranial site was selected for placement of the active electrode in performing the QEEG assessment. Prior studies [24, 30] had also indicated that differentiation between groups occurred when participants were involved in scholastic tasks (e.g., reading, listening, drawing), as would have been expected. Therefore, the difficulty sustaining attention during completion of these types of tasks (as manifested on the QEEG testing) provides a neurometric index for identifying the presence and degree of ADHD.

Figure 1:
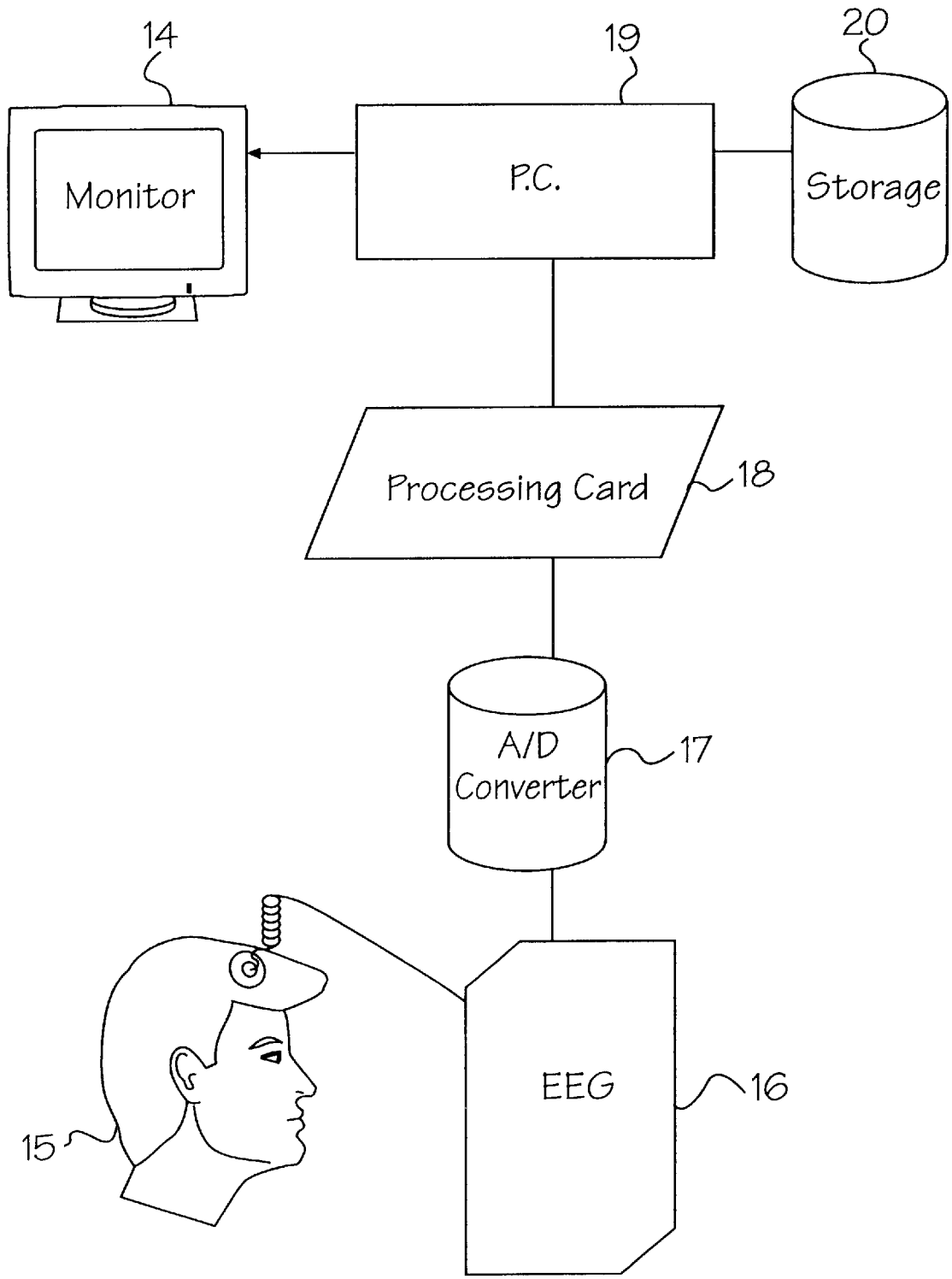
FIG. 1 illustrates a block diagram of the office apparatus used for ADHD testing using the simplified, inventive QEEG process.

Referring to FIG. 1, the testing apparatus of this invention is illustrated. A VGA monitor 14 is used to observe the testing being performed. The monitor 14 is connected to a personal computer 19, having a minimum 486 operating system. The computer 19 is connected to a digital processing card 18 (contained in an Autogenics A-620 instrument) and an Analog-to-Digital converter 17 (Stoelting Autogenics Part No. 7000-08) that is connected to a Single Channel, Dual Frequency EEG 16 (Autogenics A-620 EEG instrument). The computer 19 is also connected to a computer storage site 20 containing the normative index data base.

The basis of this invention involves obtaining QEEG recordings using the single channel EEG recording device 16. The computer 19 is programmed to select and statistically analyze specific EEG frequency bands. The EEG 16 and the associated software for programming the computer 19 consist of an Autogenics A-620 electroencephalograph with associated assessment software provided by the Stoelting-Autogenics Company located in Wood Dale, Ill. The individual 15 is connected to the single channel EEG device 16 via a monopolar (referential) EEG cable with junction box (Autogenics Part No. 800-032 M), not shown.

This system provides clinicians with a quantitative analysis of electrophysiological recordings in two frequency bands: theta (4–8 Hz) and beta (13–21 Hz). Four short periods (90 seconds each) of digitized EEG are obtained. A Fast Fourier Transformation algorithm, commonly utilized in this field, is used to process the signals and transform them into the data required for evaluation of ADHD.

Figure 2A:
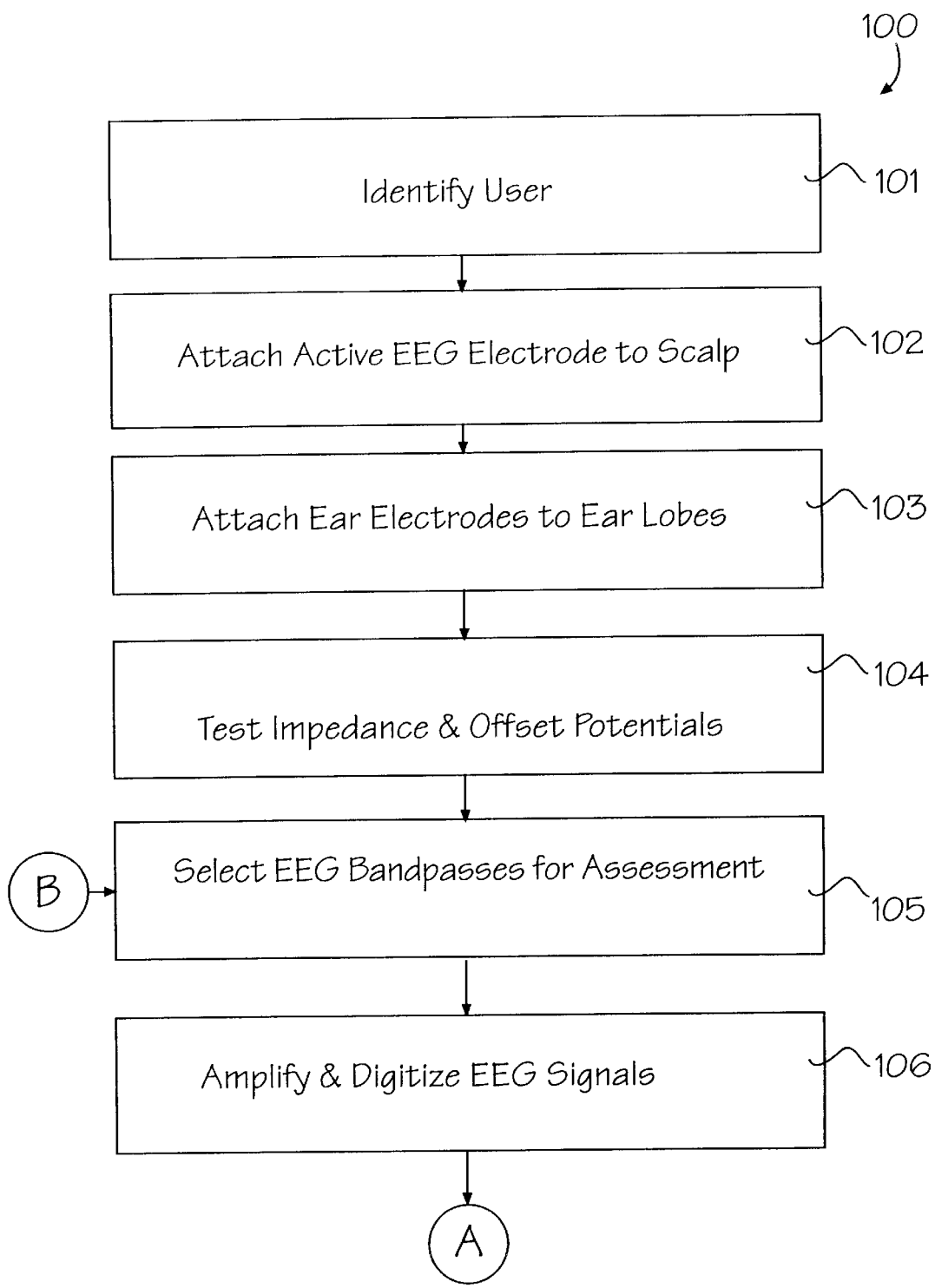
FIGS. 2a and 2b depict a flow chart diagram of the method of this invention.
Figure 2B:
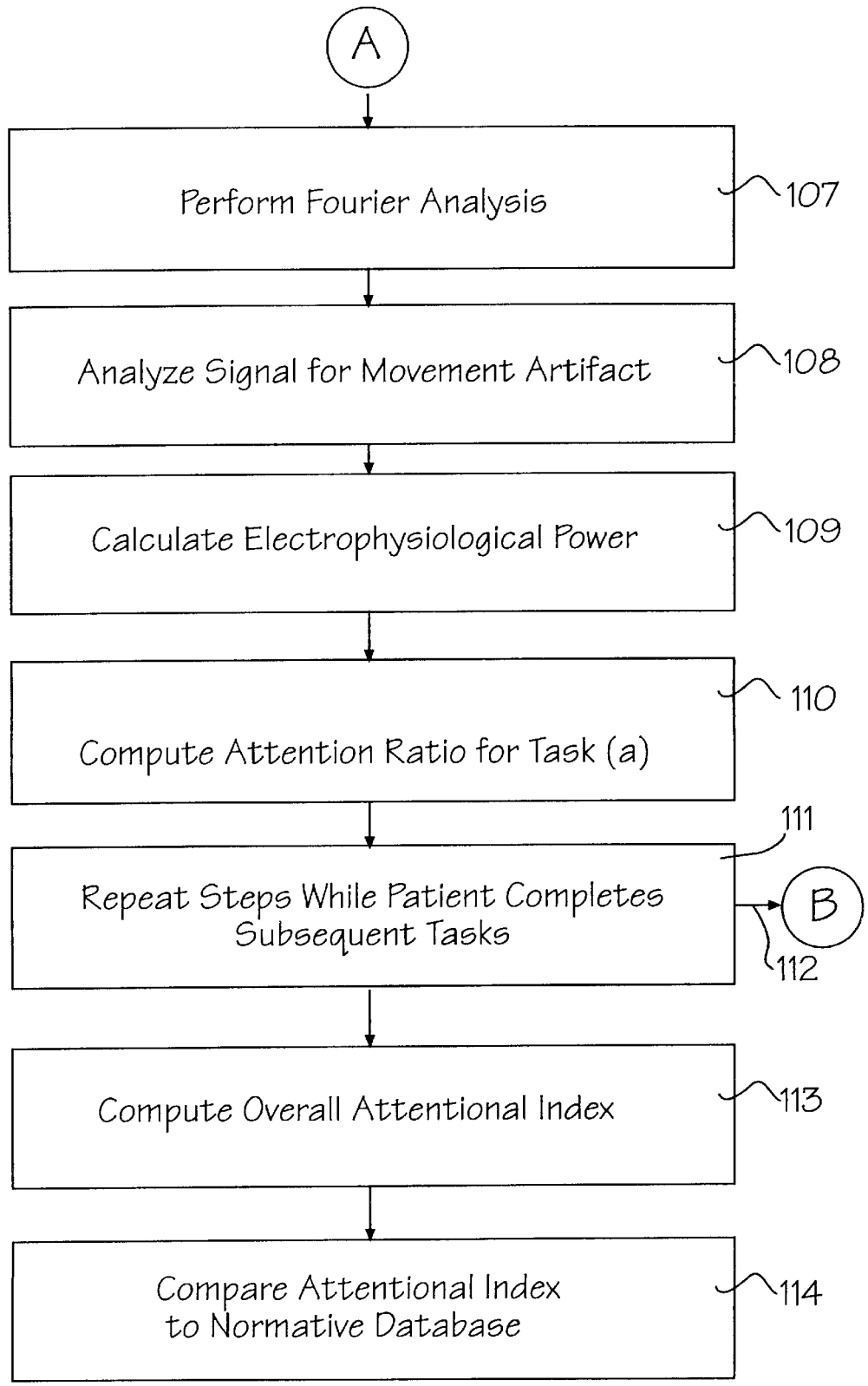

Referring to FIGS. 2a and 2b, a flow chart 100 depicts the sequential steps of the testing method for quantitatively diagnosing and evaluating ADHD in individuals using the apparatus shown in FIG. 1. The individual being tested is prepared, step 101, and the EEG electrode is attached to the scalp at cranial site Cz, step 102. Thereafter, ear electrodes are attached to the individual's ear lobes, step 103. Impedance and offset potentials are obtained, step 104. Particular EEG frequency bands are then selected for the ADHD assessment, step 105. The EEG signals are amplified and digitized, step 106 during a 90 second period, in which the individual maintains an eyes open fixed gaze. Then a Fourier analysis of the signals is obtained, step 107. The signal is analyzed for muscular and ocular movement artifact, step 108. The computer 19 (FIG. 1) then processes the data and calculates the electrophysiological power (pW) recorded at 4–8 Hz and 13–21 Hz, step 109, as well as a ratio of power (theta/beta) at these frequencies, step 110.

The individual is then given a number of tasks requiring attention. From a first test, step 111, an attention ratio (theta/beta power ratio) is obtained. Additional attention tasks are given to the individual, step 111, which require repetition of steps 105 through 110, as shown by exit line 112 and flow chart connector B. Thereafter, the overall neurometric index is computed, step 113. The tested index obtained in step 113 is then compared to a normative database index that has been determined during investigations conducted by the inventors, step 114.

Example of a Typical Test Procedure

The following is a more detailed step-by-step description of a typical test procedure used in this invention.

1. The vertex (Cz) is located using the International 10–20 system of electrode placement.

2. The area is cleaned using Omni prep (or equivalent) and Isopropyl alcohol. A small amount of conductive paste (e.g., Ten 20) is applied to the scalp and a Grass Gold Disc Electrode with hole (E5GH) and the sensor are attached to the scalp. A similar cleaning procedure is used for preparing the ear lobes. One pair of Gold Disc Electrodes in Ear Clip (Grass E34D) is attached to each ear lobe. Quality of preparation is assessed via an Autogenics Electrode Tester. Impedance reading is set below 10 KOhms. Offset potential is set below 10 mv before recordings are obtained.

3. Band frequencies are selected with 4–8 Hz defined as theta and 13–21 Hz defined as beta. Once the sensors are tested and band frequencies defined, the individual's electrophysiological activity at Cz is recorded during the following 90 second tasks:

a) Eyes Fixed Baseline: The patient is seated in front of the computer monitor display and instructed to focus his/her gaze on the monitor's "on/off" indicator light. EEG recordings are obtained for 90 seconds. After the task is completed, the EEG record is reviewed in two second intervals ("epochs") in order to manually filter out epochs containing excessive EMG artifact (e.g., body movement, eye rolls or blinks). A minimum of 15 low artifact epochs (i.e., no evidence of eye rolls/blinks and peak EMG output below 15 mv) is required for completion of this task.

b) Silent Reading: The next 90 second task is reading. Material that is age or grade appropriate is selected from school reading texts, reading tasks from the Kaufman Test of Educational Achievement, the Peabody Individual Achievement Test, or other age-related reading tests, and the material is read silently by the patient. Again, after completion of this task, the EEG is reviewed in two second intervals to eliminate epochs with excessive EMG activity or eye movement/blink artifact. A minimum of 15 low artifact epochs is required for completion of this assessment task.

c) Listening: A 90 second listening task occurs next. Age appropriate material is selected and read by a clinician, as described for Task (b), above. EEG review is conducted, as with Tasks (a) and (b).

d) Drawing: A stable drawing surface is placed in front of the individual. The person is instructed to copy geometric figures from one of the following tests: Beery-Bender Gestalt, Benton Visual Retention Test, McCarthy Scales of Child Development. Electrophysiological activity is recorded for 90 seconds with review, as for the aforementioned tasks.

After the data is collected, a statistical analysis is performed. The analysis is first conducted by task and a ratio of electrophysiological power produced and recorded at 4–8 Hz is divided by the power recorded at 13–21 Hz. A separate ratio is calculated for each task. Finally, an average ratio for the four tasks is calculated and an Attentional Index is derived. It is this Attentional Index that is used for comparison with the normative database.

The specifications of the equipment used in the development of the current invention were as follows: Signal acquisition was obtained using the aforementioned A-620 EEG device. Input was Single Channel, Dual Frequency. Gain was 50,000. Noise was less than 1 mv PP, referred to input. Differential Input Impedance was 200 KOhms. Common Mode Rejection Ratio was greater than 100 db. Amplitude Range was 1–100 mv, RMS. EEG frequency bands that could be recorded with this equipment ranged from 1.0 Hz to 32 Hz. Sampling rate was 128. A/D resolution was 12 bits (0.05 mv). EMG was also recorded with the A-620 EEG device (band pass frequency was 100–300 Hz, fixed). Computer requirements were a PC, the minimum requirement being a 486 machine.

Test Results

In order to assess the ability of this invention to meet the standards for a valid and reliable assessment process, a series of studies have been conducted by the inventors [30]. Although in the initial study [24], the inventors established a database founded on a QEEG examination of 482 individuals, cross validation, construct validation and test-retest reliability studies were required. For these reasons, five additional studies were conducted [30].

In the first study, the inventors compared the QEEG derived Attentional Index of 96 individuals diagnosed with ADHD and 33 "non-clinical" controls, none of whom had participated in the initial validation study. This study was intended as a cross-validation study with non-clinical controls. ANOVA results indicated significant differences between the two groups (ADHD vs. Control), with cortical slowing noted in members of the ADHD, Inattentive and the ADHD, Combined groups. Using the critical values for cortical slowing established in the normative study as the basis for classification as ADHD or non-ADHD, 93% of the individual participants were accurately classified.

Next, the QEEG derived Attentional Index was examined in 155 participants. Of these individuals, 129 were classified as ADHD, using the selection criteria developed in the initial study [24]; 13 individuals were classified with Depressive Disorders and 13 were classified with an Oppositional Defiant Disorder based on rating scales and DSM-IV criteria. None of these individuals had participated in the initial validation study. Significant differences were again noted in the results of the QEEG data, with cortical slowing only noted in the ADHD groups. Classification as ADHD or non-ADHD was accurate for 94% of the participants. It was considered significant that the results of this study demonstrated that common co-morbid conditions, such as Depression and Oppositional Defiant Disorders, are not characterized by cortical slowing on the EEG.

It was also considered significant that the absence of cortical slowing in the QEEG's of patients diagnosed with Oppositional Defiant Disorders and Depression is consistent with PET and SPECT findings. Amen and Carmichael [31], using SPECT, reported increased activity in the anterior medial aspects of the frontal lobes in patients diagnosed with Oppositional Defiant Disorder. Previously, Hollander [32], Machlin [33], Mordahl [34] and Swedo [35] reported a similar pattern of increased metabolic activity, bilaterally, in the anterior medial portions of the frontal lobes on PET and SPECT examinations of patients diagnosed with affective disorder. As in the inventors' QEEG studies, cortical slowing was not observed in PET or SPECT procedures examining patients diagnosed with an affective or oppositional disorder.

In order to assess the "construct" validity of their QEEG process, the inventors next examined the degree of diagnostic agreement between classification based on the Attentional Index and that derived from a CPT (the Test of Variables of Attention). In this study 155 individuals were examined (the same participants as described above). As reported previously, 129 of these participants were classifiable with ADHD, the remainder as either Depressed or with Oppositional Defiant Disorder. Agreement between classification determined by the CPT and the QEEG was noted in 88% of the participants. The degree of agreement was significant ($p<0.001$).

In the fourth study, 83 participants classifiable as ADHD using the previously described selection criteria and 18 clinical controls (9 with Depressive Disorders, 9 with Oppositional Defiant Disorder) were evaluated with the QEEG screening procedure as well as the ADDES. Consistency between the two measures was assessed. The rate of agreement was 83% ($p<0.001$). Overall, the results of the construct validation studies provided further support for the QEEG measure as a laboratory test for ADHD.

Finally, the inventors reported a test-retest reliability study of 55 individuals who met research criteria for classification as either ADHD, Inattentive or Combined Types. These individuals were evaluated on two occasions. During each assessment session, the QEEG scanning procedure for ADHD was conducted over four conditions (eyes open baseline, reading, listening, drawing). Each condition was 90 seconds in duration. An Attentional Index was calculated as in previous studies and the consistency of this index over the two testing sessions (conducted 30 days apart) was calculated. The correlation coefficient ($r=0.96$) revealed a significant level of consistency ($p<0.01$) between the two QEEG-derived attentional indices.

REFERENCES

[1] Barkley, R. A. (1998). *Attention-Deficit Hyperactivity Disorder: A Handbook for Diagnosis and Treatment*, (2nd Edition). New York: Guilford Press.

[2] American Psychiatric Association. (1994). *Diagnostic and Statistical Manual of Mental Disorders*, (4th Edition). Washington, D.C.: Author.

[3] Zametkin, A. J., Ernst, M., & Silver, R. (1998). Laboratory and diagnostic testing in child and adolescent psychiatry: A review of the past 10 years. *Journal of the American Academy of Child and Adolescent Psychiatry*, 37, 464–472.

[4] Barkley, R. A., McMurray, M. B., Edelbrock, C. S., & Robbins, K. (1990). The side effects of Ritalin: A systematic placebo controlled evaluation of two doses. Pediatrics, 86, 184–192.

[5] Swanson, J. M., McBurnett, K., Christian, D. L., & Wigal, T. (1995). Stimulant medications and the treatment of children with ADHD. In T. H. Ollendick & R. J. Prinz (Eds.), *Advances in Clinical Child Psychology* (vol. 17, pp. 265–322). New York: Plenum.

[6] Achenbach, T. M., & Edelbrock, C. S. (1983). *Manual for the Child Behavior Profile and Child Behavioral Checklist*. Burlington, Vt.: Author.

[7] Conners, C. K. (1969). A teacher rating scale for use in drug studies with children. *American Journal of Psychiatry*, 126, 884–888.

[8] DuPaul, G. J. (1990). *The ADHD Rating Scale: Normative Data, Reliability and Validity*. Worcester: University of Massachusetts Medical Center.

[9] McCarney, S. B. (1989) *Attention Deficit Disorders Evaluation Scale*. Columbia, Mo.: Hawthorne.

[10] Conners, C. K. (1994). *Conners' Continuous Performance Test Manual*. Toronto: Multi-Health Systems, Inc.

[11] Greenberg, L. M. (1994). *T.O.V.A. Continuous Performance Test Manual*. Los Alamatos, Calif.: Universal Attention Disorders.

[12] Sanford, J. A. (1994). *IVA Manual*. Richmond, Va.: BrainTrain.

[13] Blondis, T. A., Accardo, P. J., & Snow, J. H. (1989). Measures of attention deficit: I. Questionnaires. *Clinical Pediatrics*, 28, 222–228.

[14] Corkum, P. V., & Siegel, L. S. (1993). Is the Continuous Performance Task a valuable research tool for use with children with attention-deficit-hyperactivity disorder? *Journal of Child Psychology & Psychiatry & Allied Disciplines*, 34, 1217–1239.

[15] Casey, B. J., Castellanos, F. X., Giedd, J. N., Marsh, W. L., Hamburger, S. D., Schubert, A. B., Vauss, Y. C., Vaituzis, A. C., Dickstein, D. P., Sarfatti, S. E., & Rapoport, J. L. (1997). Implication of right frontostriatal circuitry in response inhibition and attention-deficit/hyperactivity disorder. *Journal of the American Academy of Child and Adolescent Psychiatry*, 36, 374–383.

[16] Zametkin, A. J., Nordahl, T. E., Gross, M., King, A. C., Semple, W. E., Rumsey, J., Hamburger, S., & Cohen, R. M. (1990), Cerebral glucose metabolism in adults with hyperactivity of childhood onset. *New England Journal of Medicine*, 323, 1361–1366.

[17] Amen, D. G., Paldi, J. H., & Thisted, R. A. (1993). Evaluating ADHD with brain SPECT imaging. *Journal of the American Academy of Child and Adolescent Psychiatry*, 32, 1081–1091.

[18] Hynd, G. W., Hern, K. L., Novey, E. S., Eliopulos, D., Marshall, R., Gonzalez, J. J., & Voeller, K. K. (1993). Attention deficit hyperactivity disorder and asymmetry of the caudate nucleus. *Journal of Child Neurology*, 8, 339–347.

[19] Semrud-Clikeman, M., Filipek, P. A., Biederman, J., Steingard, R., Kennedy, D., Renshaw, P., & Bekken, K. (1994). Attention-deficit hyperactivity disorder: Magnetic resonance imaging morphometric analysis of the corpus callosum. *Journal of the American Academy of Child and Adolescent Psychiatry*, 33, 875–881.

[20] Castellanos, F. X., Giedd, J. N., Eckburg, P., Marsh, W. L., Vaituzis, C., Kaysen, D., Hamburger, S. D., & Rapoport, J. L. (1994). Quantitative morphology of the caudate nucleus in attention deficit hyperactivity disorder. *American Journal of Psychiatry*, 151, 1791–1796.

[21] Castellanos, F. X., Giedd, J. N., Marsh, W. L., Hamberger, S. D., Vaituzis, A. C., Dickstein, D. P., Sarfatti, S. E., Vauss, Y. C., Snell, J. W., Lange, N., Kaysen, D., Krain, A. L., Ritchie, G. F., Rajapakse, J. C., & Rapoport, J. L. (1996). Quantitative brain magnetic resonance imaging in attention-deficit hyperactivity disorder. *Archives of General Psychiatry*, 53, 607–616.

[22] Mann, C. A., Lubar, J. F., Zimmerman, A. W., Miller, B. A., & Nuenchen, R. A. (1992). Quantitative analysis of EEG in boys with attention deficit/hyperactivity disorder (ADHD). A controlled study with clinical implications. *Pediatric Neurology*, 8, 30–36.

[23] Chabot, R. A., & Serfontein, G. (1996). Quantitative electroencephalographic profiles of children with attention deficit disorder. *Biological Psychiatry*, 40, 951–963.

[24] Monastra, V. J., Lubar, J. F., Linden, M., VanDeusen, P., Green, G., Wing, W., Phillips, A., & Fenger, T. N. (1998). Assessing ADHD via quantitative electroencephalography: An initial validation study. *Neuropsychology*, In press.

[25] Lubar, J. F. (1997) Neocortical dynamics: Implications for understanding the role of neurofeedback and related techniques for the enhancement of attention. *Applied Psychophysiology and Biofeedback*, 22, 111–126.

[26] Sterman, M. B. (1996). Physiological origins and functional correlates of EEG rhythmic activities: Implications for self-regulation. *Biofeedback and Self-Regulation*, 21, 3–33.

[27] Lubar, J. F., Bianchini, K. I., Calhoun, W. H., Lambert, E. W., Brody, Z. H., & Shabsin, H. W. (1985). Spectral analysis of EEG differences between children with and without learning disabilities. *Journal of Learning Disabilities*, 18, 403–408.

[28] Cooley, J. W., & Tukey, J. W. (1965). An algorithm for the machine calculation of complex Fourier series. *Mathematics of Computation*, 19, 267–301.

[29] Lubar, J. F., Swartwood, M. O., Swartwood, J. N., & Timmermann, D. L. (1996). Quantitative EEG and auditory event-related potentials in the evaluation of attention-deficit/ hyperactivity disorder: Effects of methylphenidate and implications for neurofeedback training. *Journal of Psycho-educational Assessment* (Monograph: Assessment of Attention-Deficit/HyPeractivity Disorders, pp. 143–204).

[30] Monastra, V. J., Lubar, J. F., & Linden, M. (1998). Assessing ADHD via quantitative electroencephalography: Test validation and reliability studies. Presented at CH.A.D.D.'s Tenth Annual Conference, New York. Paper in preparation.

[31] Amen, D. G., & Carmichael, B. A. (1997). Oppositional children similar to OCD on SPECT: Implications for treatment. *Journal of Neurotherapy*, 2, 1–7.

[32] Hollander, E. (1992). Hyperfrontality and serotonin in OCD. Presented at the Annual Meeting of the *American Psychiatric Association*.

[33] Machlin, S. R., Harris, G. J., Peralson, G. D. (1991). Elevated medial-frontal cerebral blood flow in obsessive-compulsive patients: A SPECT study. *American Journal of Psychiatry*, 148, 1240–1242.

[34] Nordahl, T. E., Benkelfat, C., & Semple, W. E. (1989). Cerebral glucose metabolic rates in obsessive compulsive disorder. *Neuropsychopharmacology*, 2, 23–38.

[35] Swedo, S. E., Schapiro, M. B., & Grady, C. L. (1989). Cerebral glucose metabolism in childhood onset obsessive compulsive disorder. *Archives of General Psychiatry*, 46, 518–523.

Since other modifications and changes varied to fit particular operating requirements and environments will be apparent to those skilled in this scientific field, the invention is not considered limited to the example chosen for purposes of disclosure and covers all changes and modifications which do not constitute departures from the true spirit and scope of this invention.

Having thus described the invention, what is desired to be protected by Letters Patent is presented in the subsequently appended claims.

What is claimed is:

1. A quantitative electroencephalographic technique for testing and assessing individuals for Attention Deficit Hyperactivity Disorder (ADHD), comprising the steps of:
   a) placing an electrode at a single cranial site of an individual to be tested for ADHD;
   b) obtaining digitized EEG data in two frequency bands: theta (4–8 Hz) and beta (13–21 Hz);
   c) obtaining a baseline neurometric index comprising a ratio of the electrophysiological power recorded in the theta band divided by the electrophysiological power recorded in the beta band obtained in step (b);
   d) thereafter, testing said individual in accordance with steps (b) and (c) under conditions requiring attentive behavior;
   e) obtaining an overall Attentional Index for said individual which represents the average theta/beta power ratio calculated during said baseline and said attentive behavior tasks; and
   f) comparing said Attentional Index obtained in step (e) to a normative database of individuals without ADHD to determine presence and severity of said individual's ADHD.

2. The quantitative technique for testing and assessing individuals for ADHD in accordance with claim 1, wherein said behavioral testing in step (d) comprises testing said individual during a reading task.

3. The quantitative technique for testing and assessing individuals for ADHD in accordance with claim 1, wherein said behavioral testing in step (d) comprises testing said individual during a listening task.

4. The quantitative technique for testing and assessing individuals for ADHD in accordance with claim 1, wherein said behavioral testing in step (d) comprises testing said individual during a drawing task.

5. The quantitative technique for testing and assessing individuals for ADHD in accordance with claim 1, further comprising the step of:
   g) utilizing a fast Fourier analysis to transform said data obtained in step (b).

6. The quantitative technique for testing and assessing individuals for ADHD in accordance with claim 1, wherein said baseline neurometric index is obtained while said individual gazes fixedly at a point.

7. The quantitative technique for testing and assessing individuals for ADHD in accordance with claim 1, further comprising the step of:
   g) placing at least one reference ear electrode on said individual.

8. Apparatus for quantitative testing and assessing individuals for Attention Deficit Hyperactivity Disorder (ADHD), comprising:
   a monitor for displaying EEG data;
   an EEG device operatively connected to said monitor and to an individual under evaluation for ADHD, said EEG device providing signals representative of the cortical electrophysiological activity of said individual;
   a processor disposed between said monitor and said EEG device, said processor being programmed to process said signals and to provide a neurometric Attentional Index for said individual; and
   storage means operatively connected to said processor for providing a comparison between a normative database and the said Attentional Index for said individual, to determine the presence and to quantify the severity of ADHD thereof.

9. The apparatus for quantitative testing and assessing individuals for ADHD in accordance with claim 8, further comprising an analog-to-digital converter disposed between said processor and said EEG device.

10. The apparatus for quantitative testing and assessing individuals for ADHD in accordance with claim 8, further comprising a digital processing card disposed between said processor and said EEG machine.

11. The apparatus for quantitative testing and assessing individuals for ADHD in accordance with claim 8, wherein said individual is connected to said EEG device at a single active cranial site.

12. The apparatus for quantitative testing and assessing individuals for ADHD in accordance with claim 11, wherein said single, active cranial site comprises the Cz site, the vertex.

13. The apparatus for quantitative testing and assessing individuals for ADHD in accordance with claim 11, wherein said individual is connected to said EEG device at at least one ear lob for obtaining a reference signal.

* * * * *